(12) United States Patent
Tabuchi et al.

(10) Patent No.: US 9,610,004 B2
(45) Date of Patent: Apr. 4, 2017

(54) ENDOSCOPE APPARATUS WITH POWER GENERATING SECTION AND PROTECTION CIRCUIT

(71) Applicant: OLYMPUS CORPORATION, Tokyo (JP)

(72) Inventors: Koichiro Tabuchi, Tokyo (JP); Makoto Ono, Sagamihara (JP); Hidekazu Shinano, Center Valley, PA (US); Mitsutaka Nemoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/849,081

(22) Filed: Sep. 9, 2015

(65) Prior Publication Data

US 2015/0374204 A1 Dec. 31, 2015

Related U.S. Application Data

(63) Continuation of application No. PCT/JP2014/069947, filed on Jul. 29, 2014.

(30) Foreign Application Priority Data

Aug. 9, 2013 (JP) ................................. 2013-166333

(51) Int. Cl.
 *A61B 1/00* (2006.01)
 *A61B 1/04* (2006.01)
 (Continued)

(52) U.S. Cl.
 CPC ...... *A61B 1/00032* (2013.01); *A61B 1/00006* (2013.01); *A61B 1/00027* (2013.01);
 (Continued)

(58) Field of Classification Search
None
See application file for complete search history.

(56) References Cited

U.S. PATENT DOCUMENTS 5,400,267 A * 3/1995 Denen ................... A61B 17/00
128/908
6,313,868 B1 * 11/2001 D'Alfonso ........... A61B 1/0002
348/72

(Continued)

FOREIGN PATENT DOCUMENTS

EP  2520215 A1  11/2012
EP  2666401 A1  11/2013
(Continued)

OTHER PUBLICATIONS

International Search Report dated Oct. 21, 2014 issued in PCT/JP2014/069947.

(Continued)

*Primary Examiner* — John P Leubecker
(74) *Attorney, Agent, or Firm* — Scully, Scott, Murphy & Presser, P.C.

(57) ABSTRACT

An endoscope apparatus is provided with: a power generating section supplying power to a target circuit of an endoscope; a scope information acquiring section acquiring scope information about the endoscope from the endoscope; a protection circuit provided in association with the power generating section, the protection circuit being capable of operating in a plurality of protection modes; and an operation controlling section controlling the power generating section, and selecting and setting one protection mode from among the plurality of protection modes for the protection circuit, based on the scope information.

5 Claims, 6 Drawing Sheets

(51) Int. Cl.
*G02B 23/24* (2006.01)
*A61B 1/045* (2006.01)
*H04N 7/18* (2006.01)
*H04N 5/225* (2006.01)

(52) U.S. Cl.
CPC ............... *A61B 1/04* (2013.01); *A61B 1/045* (2013.01); *G02B 23/2476* (2013.01); *A61B 1/00059* (2013.01); *H04N 7/185* (2013.01); *H04N 2005/2255* (2013.01)

(56) References Cited

U.S. PATENT DOCUMENTS

| | | | |
|---|---|---|---|
| 6,638,212 B1* | 10/2003 | Oshima | A61B 1/0002 348/72 |
| 8,045,010 B2* | 10/2011 | Yoshida | H04N 5/23209 348/211.14 |
| 2002/0156349 A1* | 10/2002 | Yamaki | A61B 1/00059 600/178 |
| 2006/0020168 A1* | 1/2006 | Naruse | A61B 1/00027 600/179 |
| 2007/0100202 A1* | 5/2007 | Murata | A61B 1/00059 600/109 |
| 2008/0027284 A1 | 1/2008 | Suda | |
| 2009/0209818 A1* | 8/2009 | Higuchi | A61B 1/00059 600/118 |
| 2012/0178992 A1 | 7/2012 | Fujimoto et al. | |
| 2013/0265403 A1 | 10/2013 | Okawa et al. | |
| 2015/0138328 A1* | 5/2015 | Yokohama | A61B 1/00018 348/65 |
| 2015/0280550 A1* | 10/2015 | Minakuchi | H02M 3/04 348/65 |

FOREIGN PATENT DOCUMENTS

| | | |
|---|---|---|
| JP | H07-194530 A | 8/1995 |
| JP | 2010-088656 A | 4/2010 |
| JP | 2012-011143 A | 1/2012 |
| WO | WO 2012/008259 A1 | 1/2012 |
| WO | WO 2013/042647 A1 | 3/2013 |

OTHER PUBLICATIONS

Extended Supplementary European Search Report dated Nov. 3, 2016 in related European Patent Application No. 14 83 5139.8.

* cited by examiner

ENDOSCOPE APPARATUS WITH POWER GENERATING SECTION AND PROTECTION CIRCUIT

CROSS REFERENCE TO RELATED APPLICATION

This application is a continuation application of PCT/JP2014/069947 filed on Jul. 29, 2014 and claims benefit of Japanese Application No. 2013-166333 filed in Japan on Aug. 9, 2013, the entire contents of which are incorporated herein by this reference.

BACKGROUND OF THE INVENTION

1. Field of the Invention

The present invention relates to an endoscope apparatus capable of power generation by a plurality of protection modes.

2. Description of the Related Art

Recently, endoscope apparatuses have been used in various fields, for example, in a medical field and an industrial field. In the medical field, an endoscope apparatus is used, for example, for observation of an organ in a body cavity, treatment using a treatment instrument and a surgical operation under endoscopic observation. An electronic endoscope configured to be capable of picking up an image of an inside of a patient's body cavity by an image pickup device is often adopted for an endoscope apparatus. The endoscope apparatus has a processor for performing video-processing of the picked-up image obtained by performing image pickup by the electronic endoscope, and the processor can convert the picked-up image to a video signal to output the video signal on a monitor or record the video signal.

The endoscope is detachably connected to the processor via a cable to provide a picked-up image to the processor and receives power supply from the processor. Japanese Patent Application Laid-Open Publication No. 2010-88656 discloses a technique for acquiring ID information about an electronic endoscope connected to a processor and generating power supply voltage suitable for the endoscope.

Various kinds of scope circuits, such as an image pickup device, sensors and various kinds of actuators, are configured in the electronic endoscope, and the processor has a plurality of kinds of power supply circuits in order to perform power supply suitable for each of the various kinds of scope circuits. Further, the processor is provided with a protection circuit for overcurrent protection and the like in order to prevent an abnormal operation, such as heat generation on a distal end and a fault in the endoscope.

How to provide protection, such as overcurrent protection, differs for each kind of scope circuit. For example, there is a case where a scope circuit immediately shuts down when a predetermined current is exceeded, a case where voltage is caused to drop so that a predetermined or larger current does not flow, and the like. Therefore, it is necessary to provide the processor with a protection circuit for each power supply circuit.

Recently, kinds of included scope circuits differ for each endoscope, and kinds of endoscopes connectable to the processor increase more and more.

SUMMARY OF THE INVENTION

An endoscope apparatus according to the present invention is provided with: a power generating section supplying power to a target circuit of an endoscope; a scope information acquiring section acquiring scope information about the endoscope from the endoscope; a protection circuit provided in association with the power generating section, the protection circuit being capable of operating in a plurality of protection modes; and an operation controlling section controlling the power generating section, and selecting and setting one protection mode from among the plurality of protection modes for the protection circuit, based on the scope information.

DETAILED DESCRIPTION OF THE PREFERRED EMBODIMENTS

Embodiments of the present invention will be described below in detail with reference to drawings.

First Embodiment

Figure 1:
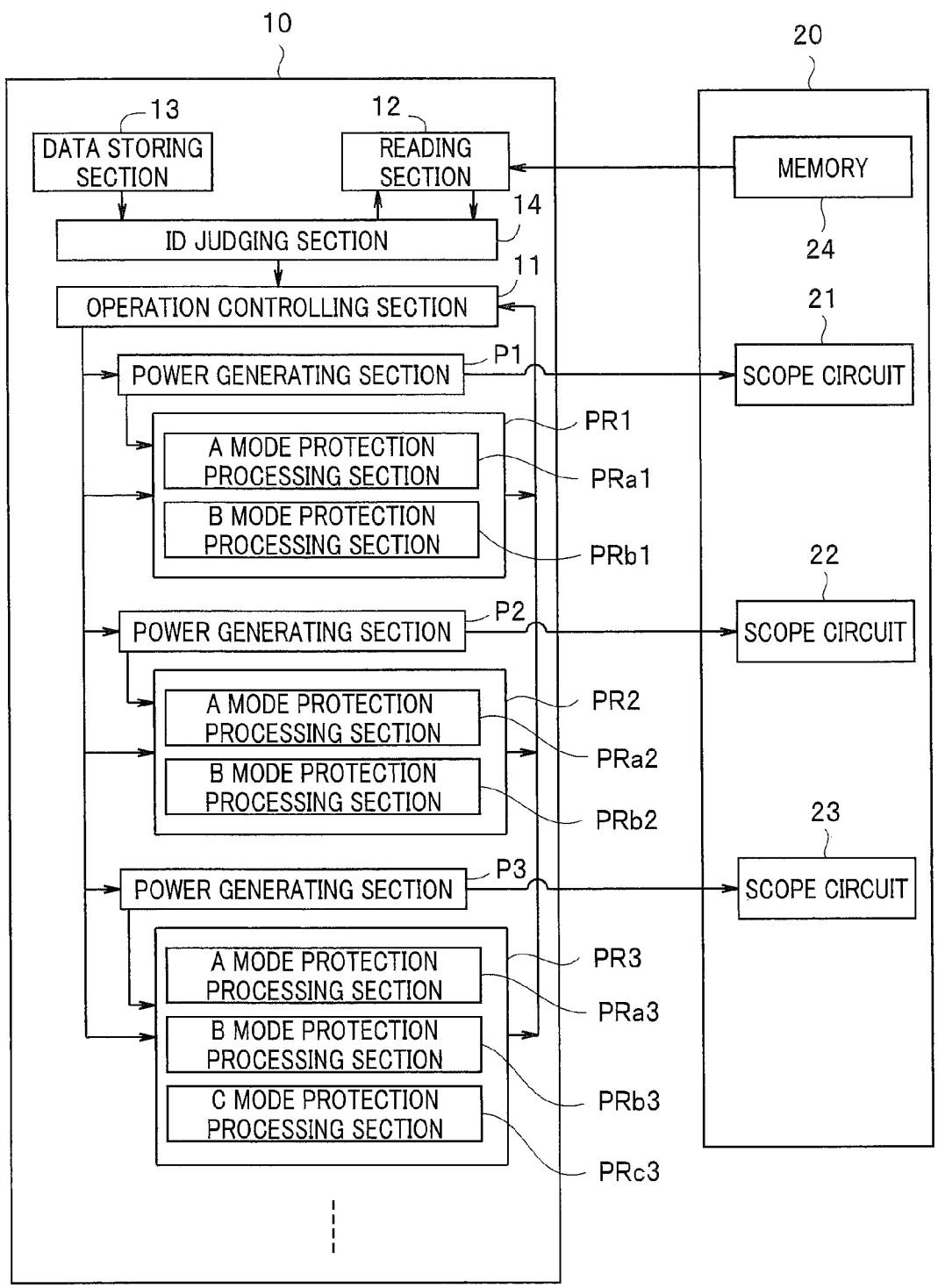
FIG. 1 is a block diagram showing an endoscope apparatus according to a first embodiment of the present invention.

FIG. 1 is a block diagram showing an endoscope apparatus according to a first embodiment of the present invention. Though the endoscope apparatus of FIG. 1 is configured with a processor 10 and an endoscope 20, not only the endoscope 20 but also other endoscopes not shown can be detachably connected to the processor 10. The endoscope 20 has scope circuits 21 to 23, which are power supply target circuits which operate in response to receiving power supply. Note that, for example, an image pickup device not shown is configured in the endoscope 20, and the image pickup device and the like which are circuits targeted by power supply are also expressed as scope circuits.

For each of the endoscopes, including the endoscope 20, kinds of the included scope circuits, a kind of a power source required for each scope circuit, and a mode of protection to be set (hereinafter referred to as a protection mode) are determined. Therefore, for example, even in a case where scope circuits included in two endoscopes, respectively, use a common power source, it is conventionally necessary to provide a processor with two power generating sections for the scope circuits if protection modes of the scope circuits are mutually different from each other.

In comparison, in the present embodiment, for example, in a case where respective scope circuits included in two endoscopes can use a common power source, one power generating section and one protection circuit are provided for the scope circuits, and a plurality of protection processing sections corresponding to the respective protection modes are switched and used in the protection circuit even when protection modes are mutually different from each other. Thereby, it is possible to reduce the number of necessary power generating sections and protection circuits.

The processor 10 is provided with a plurality of power generating section P1, P2, . . . (hereinafter also generically referred to as power generating sections P). The power generating sections P1, P2, . . . are adapted to be capable of supplying power to respective scope circuits of each connectable endoscope. In an example of FIG. 1, an example is shown that the endoscope 20 has the three scope circuits 21 to 23, and the power generating sections P1 to P3 supply power to the scope circuits 21 to 23, respectively. The power generating sections P1, P2, . . . are adapted to be capable of generating power suitable for the scope circuits 21 to 23, respectively, by being controlled by an operation controlling section 11 to be described later.

The processor 10 is provided with protection circuits PR1, PR2, . . . (hereinafter also generically referred to as protection circuit PRs) corresponding to the power generating sections P1, P2, . . . , respectively. In the present embodiment, each of the protection circuits PR1, PR2, . . . is provided with one or more protection processing sections with mutually different protection modes. In the example of FIG. 1, the protection circuit PR1 is provided with two protection processing sections PRa1, PRb1; the protection circuit PR2 is provided with two protection processing sections PRa2, PRb2; and the protection circuit PR3 is provided with three protection processing sections PRa3, PRb3, PRc3.

In the present embodiment, it is possible to arrange a desired number of protection processing sections with mutually different protection modes, in each of the protection circuits PR1, PR2, . . . . In the example of FIG. 1, a protection mode is set to, for example, an A protection mode for protection processing sections PRa1, PRa2, PRa3 (hereinafter also generically referred to as protection processing sections PRa); the protection mode is set to, for example, a B protection mode for protection processing sections PRb1, PRb2, PRb3 (hereinafter also generically referred to as protection processing sections PRb); and the protection mode is set to, for example, a C protection mode for a protection processing section PRc3 (hereinafter also referred to as protection processing section PRc).

For example, the A protection mode is a protection mode designed so that shutdown immediately works when an abnormality is detected, and the B protection mode is a protection mode set so that voltage drops without shutdown when an abnormality is detected. Further, the C protection mode is, for example, a protection mode for causing a driving power source and a driving circuit for the image pickup device to stop when an abnormality is detected.

Note that the protection mode set for each of the protection processing sections of the protection circuits PR1, PR2, . . . is an example, and the number of protection processing sections and kinds of protection modes to be set can be appropriately set.

The endoscope 20 is provided with a memory 24 storing scope IDs indicating kinds of endoscopes. A reading section 12 of the processor 10 is adapted to be capable of reading scope IDs from the memory 24 when the endoscope 20 is mounted on the processor 10, and the reading section 12 outputs the read scope IDs to an ID judging section 14. A data storing section 13 holds a power supply control parameter corresponding to each scope ID. The ID judging section 14 is adapted to be given the scope IDs read by the reading section 12, read power supply control parameters corresponding to the scope IDs from the data storing section 13 and supplies the power supply control parameters to an operation controlling section 11.

The operation controlling section 11 controls each of the power generating sections P1, P2, . . . based on the power supply control parameters to cause each of the power generating sections P1, P2, . . . to generate necessary power. Further, the operation controlling section 11 decides which of the respective protection processing sections PRa, PRb, PRc of each of the protection circuits PR1, PR2, . . . to be selected, for each of the protection circuits PR1, PR2, . . . , based on the power supply control parameters and outputs a selection signal to each of the protection circuits PR1, PR2, . . . . Thereby, the operation controlling section 11 can cause the respective protection circuits PR1, PR2, . . . to operate in protection modes based on the power supply control parameters.

The respective protection circuits PR1 to PR3 are given information about power supply such as a current and voltage supplied from the respective power generating sections P1 to P3 to the respective scope circuits 21 to 23. In each of the protection circuits PR1, PR2, . . . , only a protection processing section selected by a selection signal functions. By monitoring the information about power supply, a control signal corresponding to a protection mode set for the selected protection processing section is outputted to the operation controlling section 11. The operation controlling section 11 controls operations of the respective power generating sections P1, P2, . . . based on control signals from the respective protection circuits PR1, PR2, . . . .

Figure 2:
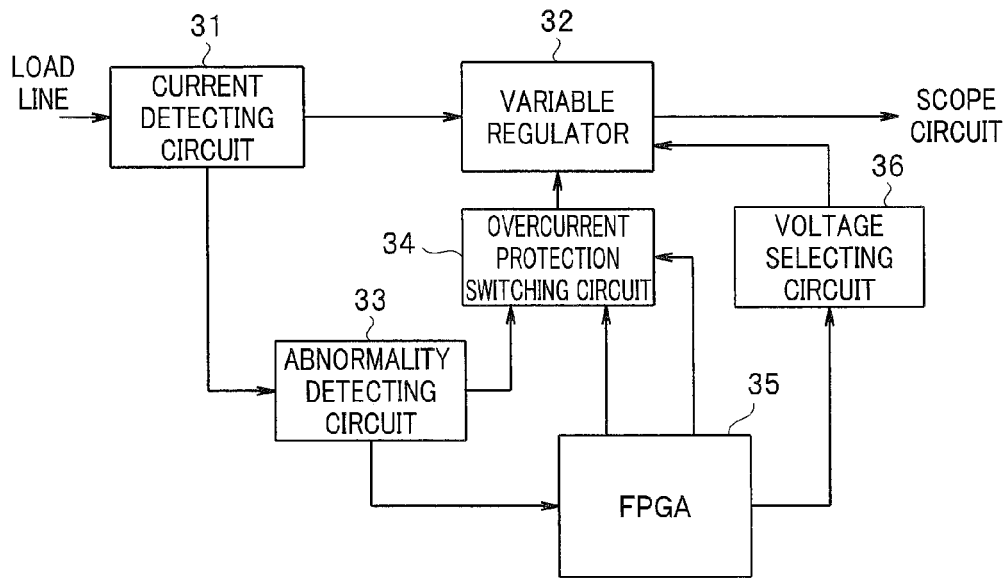
FIG. 2 is a circuit diagram showing an example of a specific configuration of main parts in the first embodiment.

FIG. 2 is a circuit diagram showing an example of a specific configuration of main parts in the present embodiment. The example of FIG. 2 shows an example of a specific configuration of the protection circuit PR1 (PR2) of FIG. 1 in which the protection processing sections PRa, PRb are configured, and shows an example of a circuit which detects an overcurrent and provides protection.

FIG. 2 shows an example where the power generating sections P1 to P3 of FIG. 1 are configured by a current detecting circuit 31, a variable regulator 32 and a voltage selecting circuit 36. Further, a field programmable gate array (hereinafter referred to as an FPGA) 35 of FIG. 2 can realize a function of the operation controlling section 11 of FIG. 1. Note that, as for only the FPGA 35 among the components of FIG. 2, a device common to all the power generating sections and protection circuits can be used.

The FPGA 35, which is the operation controlling section 11, is supplied with power supply control parameters from the ID judging section 14 (not shown) and outputs a control signal for selecting voltage which the variable regulator 32 is caused to generate, to the voltage selecting circuit 36 based on the power supply control parameters. The voltage selecting circuit 36 controls the variable regulator 32 to generate power supply voltage corresponding to the instruction by the FPGA 35.

Further, a load current detection result is inputted to the variable regulator 32 from the current detecting circuit 31. An output current of the variable regulator 32 is controlled so that a load current from the current detecting circuit 31 corresponds to a predetermined target value specified by the FPGA 35. Thus, power based on an instruction of the FPGA 35 is generated from the variable regulator 32.

In the example of FIG. 2, the protection circuits PR1, PR2, . . . of FIG. 1 are configured by an abnormality detecting circuit 33, an overcurrent protection switching circuit 34 and the FPGA 35. The abnormality detecting circuit 33 is given an output of the current detecting circuit 31, judges whether an abnormality has occurred in a load current or not, and outputs a judgment result to the overcurrent protection switching circuit 34 and the FPGA 35. The FPGA 35 is adapted to be capable of, when a judgment result indicating an abnormality in the load current is inputted from the abnormality detecting circuit 33, outputting a shutdown instruction signal for shutting down the variable regulator 32 to the overcurrent protection switching circuit 34. Thus, the judgment result of the abnormality detecting circuit 33 and the shutdown instruction signal from the FPGA 35 can be inputted to the overcurrent protection switching circuit 34.

In the present embodiment, the FPGA 35 is adapted to, when the judgment result indicating an abnormality in a load current is inputted from the abnormality detecting circuit 33, output a switching signal for causing one of the two inputs to be selectively supplied to a control end of the variable regulator 32, to the overcurrent protection switching circuit 34 based on the power supply control parameters from the ID judging section 14.

The variable regulator 32 is adapted to, when the shutdown instruction signal is inputted to the control end by the overcurrent protection switching circuit 34, shut down immediately and stop an operation. Further, the variable regulator 32 is adapted to, when the judgment result indicating an abnormality from the abnormality detecting circuit 33 is inputted to the control end by the overcurrent protection switching circuit 34, stop output and resume output when input of the judgment result indicating the abnormality stops. That is, by switching between signals to be given to the control end of the variable regulator 32, functions of both of the protection processing sections PRa, PRb are realized by the abnormality detecting circuit 33, the overcurrent protection switching circuit 34 and the FPGA 35.

Figure 3:
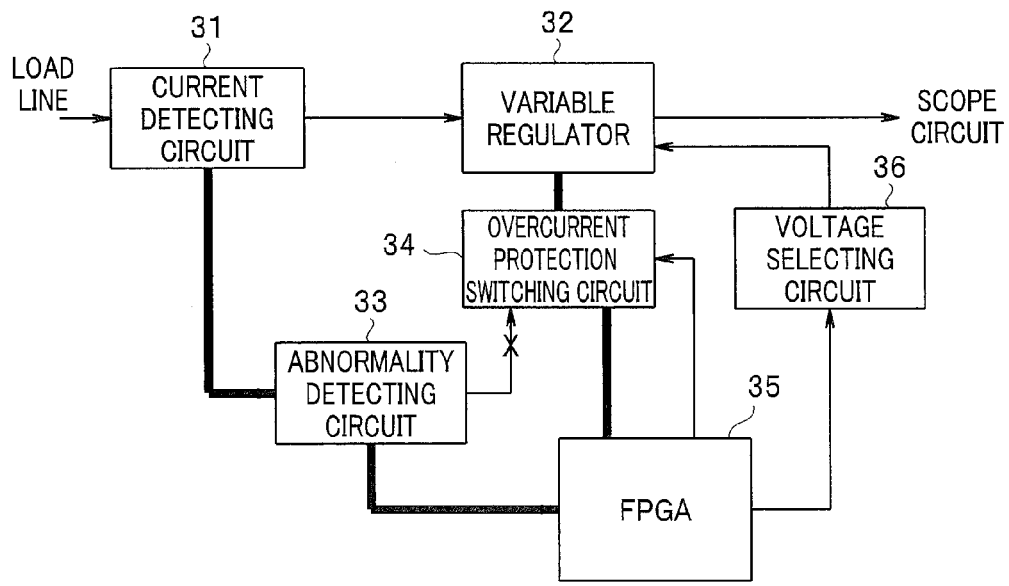
FIG. 3 is an illustration diagram for illustrating control in an A protection mode.
Figure 4:
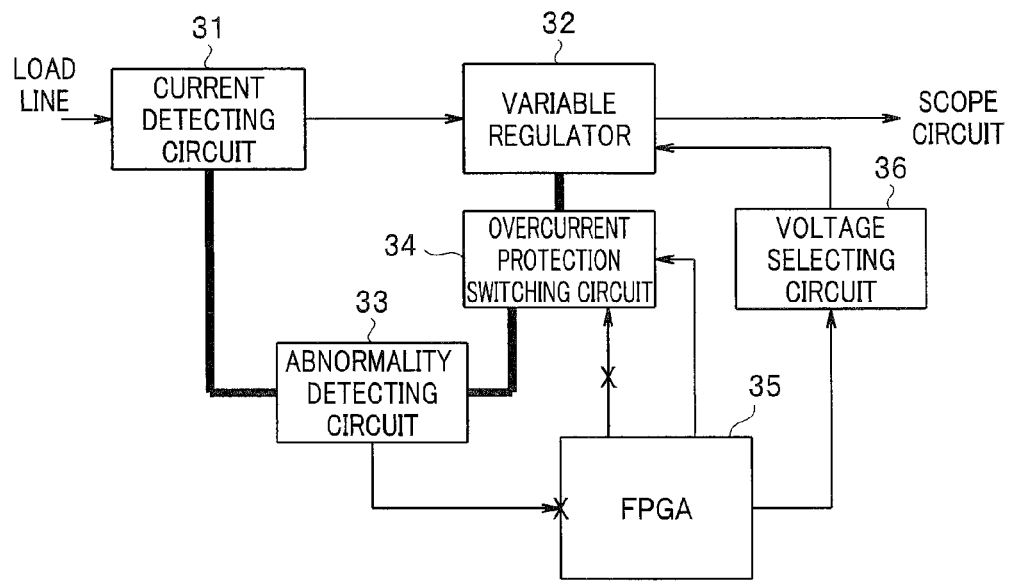
FIG. 4 is an illustration diagram for illustrating control in a B protection mode.

Next, an operation of the embodiment configured as described above will be described with reference to FIGS. 3 and 4. FIGS. 3 and 4 are illustration diagrams for illustrating control in the A and B protection modes, respectively. Note that, in FIGS. 3 and 4, a signal flow is shown by thick lines, and it is indicated by x marks that a signal is not transmitted.

Note that description will be made on an assumption that the A protection mode is a protection mode designed so that shutdown immediately works when an abnormality is detected, and the B protection mode is a protection mode designed so that voltage drops without shutdown when an abnormality is detected.

For example, for power supply to such a scope circuit that there is a possibility of causing heat generation at a distal end or the like of an endoscope insertion portion, for example, the image pickup device, the A protection mode is set. Further, as for such a scope circuit and the like that there is only a small possibility of causing heat generation at the distal end, since there may be a case where it is better to continue power supply in a constant current state even if power supply voltage decreases somewhat than to cut off power supply and cause disappearance of an image, the B protection mode is set for such a scope circuit.

When the endoscope 20 is mounted on the processor 10, the reading section 12 of the processor 10 reads scope IDs from the memory 24 and outputs the scope IDs to the ID judging section 14. The ID judging section 14 reads power supply control parameters corresponding to the scope IDs from the data storing section 13 and outputs the power supply control parameters to the FPGA 35 (the operation controlling section 11). The FPGA 35 can grasp kinds of power to be generated and protection modes for the respective scope circuits 21 to 23 of the endoscope 20 by the power supply control parameters.

Now, it is assumed that power is supplied to the scope circuit 21 in the A protection mode, and power is supplied to the scope circuit 22 in the B protection mode. If an abnormality such as an overcurrent has not occurred in power supply to the scope circuits 21, 22, the respective variable regulators 32 of the power generating sections P1 and P2 generate power supply voltages selected by the respective voltage selecting circuits 36 to supply power to the scope circuits 21, 22.

Here, it is assumed that a load current of the scope circuit 21 becomes abnormal because of a fault of the scope circuit 21 or the like. The abnormality detecting circuit 33 detects the abnormality by an output of the current detecting circuit 31 of the power generating section P1, and outputs a judgment result indicating the abnormality to the FPGA 35 and the overcurrent protection switching circuit 34.

Power is supplied to the scope circuit 21 in the A protection mode, and the FPGA 35 generates a shutdown instruction signal and causes the overcurrent protection switching circuit 34 to select the output of the FPGA 35 according to the judgment result indicating the abnormality from the abnormality detecting circuit 33.

The thick lines in FIG. 3 show such a signal flow. By detection of an overcurrent, a shutdown instruction signal from the FPGA 35 is supplied to the control end of the variable regulator 32 via the overcurrent protection switching circuit 34. Thereby, the variable regulator 32 stops output. Thus, immediately after generation of the overcurrent, shutdown is immediately performed, and power supply to the scope circuit 21 stops.

Further, it is assumed that a load current of the scope circuit 22 becomes abnormal because of a fault of the scope circuit 22 or the like. The abnormality detecting circuit 33 detects the abnormality by an output of the current detecting circuit 31 of the power generating section P2, and outputs a judgment result indicating the abnormality to the FPGA 35 and the overcurrent protection switching circuit 34.

Power is supplied to the scope circuit 22 in the B protection mode. The FPGA 35 neither accepts the judgment result of the abnormality detecting circuit 33 nor generates a shutdown instruction signal according to the judgment result indicating the abnormality from the abnormality detecting circuit 33. Further, the FPGA 35 causes the overcurrent protection switching circuit 34 to select the output of the abnormality detecting circuit 33.

The thick lines in FIG. 4 show such a signal flow. By detection of an overcurrent, a judgment result indicating an abnormality from the abnormality detecting circuit 33 is supplied to the control end of the variable regulator 32 via the overcurrent protection switching circuit 34. Thereby, the variable regulator 32 stops an output. Then, a current of a load line suddenly decreases. Then, the judgment result indicating the abnormality is not outputted from the abnormality detecting circuit 33, and the variable regulator 32 resumes output. In a case of a fault caused in the scope circuit 22 and the like, the load current shows an abnormal value again by power supply from the power generating section P2. Then, a judgment result indicating the abnormality from the abnormality detecting circuit 33 is supplied to the variable regulator 32 again, and output of the variable regulator 32 stops. A similar operation is repeated hereafter, and the load current converges to an almost fixed value. Thus, constant current control is performed immediately after occurrence of the overcurrent to prevent the occurrence of the overcurrent.

Thus, in the present embodiment, by providing a plurality of protection processing sections for each power generating section, it becomes possible to supply power in a plurality of protection modes, and it becomes possible to acquire scope IDs and select a protection mode for each power supply based on the scope IDs. Thereby, even in a case of supplying power to a plurality kinds of endoscopes, it is possible to perform power supply corresponding to each scope circuit with a relatively small number of power generating sections and protection circuits and reduce a size of the apparatus.

Second Embodiment

Figure 5:
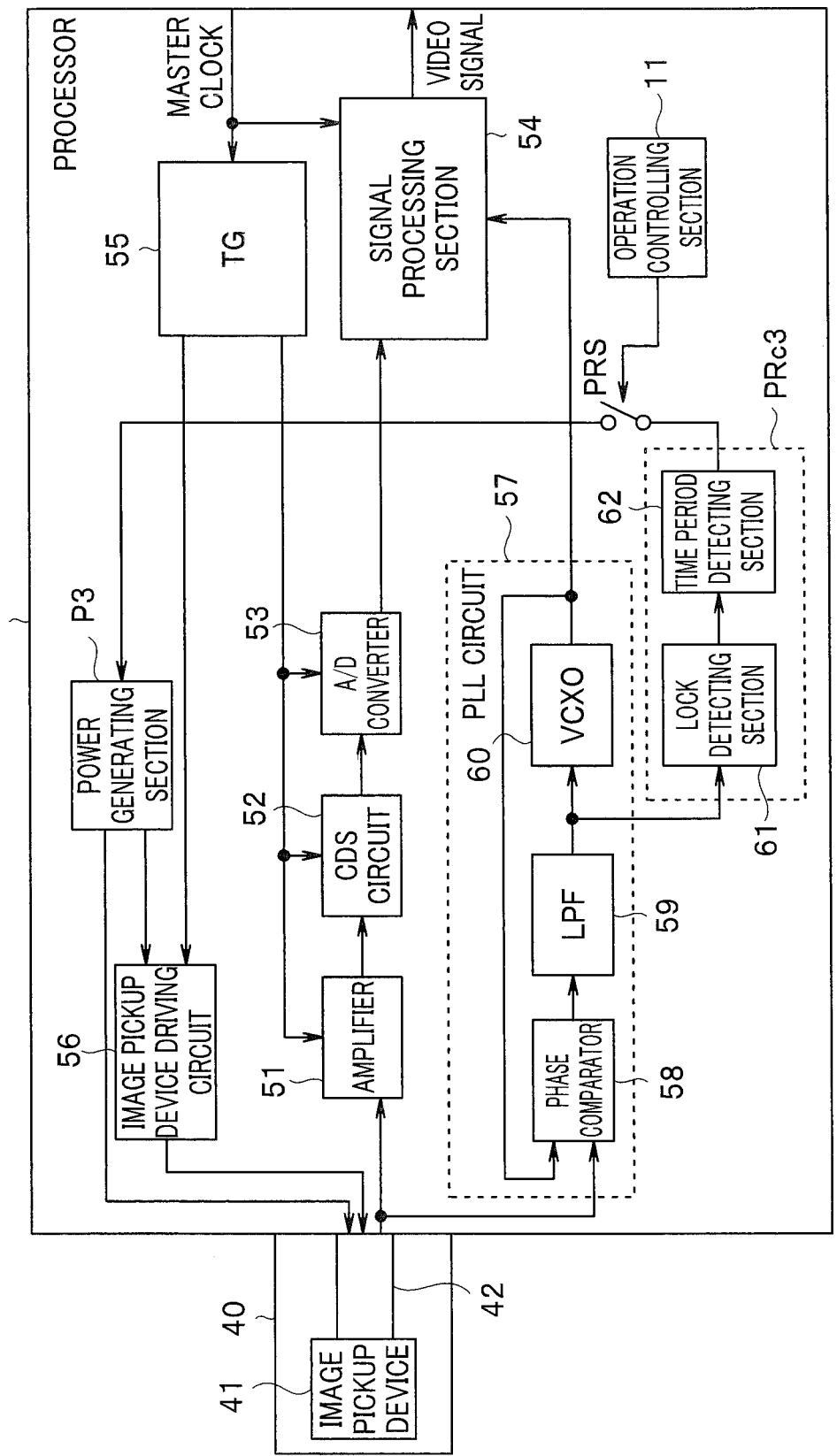
FIG. 5 is a schematic diagram showing a second embodiment of the present invention.

FIG. 5 is a schematic diagram showing a second embodiment of the present invention. The present embodiment shows another example of the protection mode. In FIG. 5, same components as those in FIG. 1 are given same reference numerals, and description thereof will be omitted.

Though a processor 50 of FIG. 5 is provided with all the components of the processor 10 of FIG. 10, power generating sections, protection circuits and the like other than parts related to a protection processing section PRc3 which provides protection in a C protection mode are not shown. Note that description will be made on an assumption that the C protection mode is, for example, a protection mode for causing the driving power source and the driving circuit for the image pickup device to stop when an abnormality is detected.

An endoscope 40 can be detachably mounted on the processor 50. An image pickup device 41 is arranged at a distal end of an insertion portion of the endoscope 40. The processor 50 has an image pickup device driving circuit 56 which supplies a drive signal to the image pickup device 41, and a power generating section P3 which supplies power to both of the image pickup device driving circuit 56 and the image pickup device 41. A master clock is inputted to the processor 50, and a timing generator (hereinafter referred to as a TG) 55 generates a timing signal for controlling each section based on the master clock. The image pickup device driving circuit 56 operates by being supplied with power from the power generating section P3 and generates a drive signal for driving the image pickup device 41 based on a timing signal from the TG 55.

An image pickup output from the image pickup device 41 is supplied to an amplifier 51. The amplifier 51 amplifies the image pickup output and outputs it to a CDS circuit 52. The CDS circuit 52 performs CDS (correlated double sampling) processing for the image pickup output. The output from the CDS circuit 52 is given to an A/D converter 53, and the A/D converter 53 converts the image pickup output to a digital signal and outputs the digital signal to a signal processing section 54. The signal processing section 54 performs predetermined signal processing for the image pickup output and generates a video signal based on the image pickup output. By giving the video signal to a monitor not shown, an endoscopic image is displayed on a display screen of the monitor.

The image pickup output from the image pickup device 41 is transmitted to the processor 50 via a scope cable 42 inserted in the endoscope 40. Depending on a cable length of the scope cable 42, phase fluctuation of the image pickup output is large. Therefore, it is necessary to use a reference signal synchronized with the image pickup output in the signal processing in the signal processing section 54. A PLL circuit 57 is given the image pickup output and generates such a reference signal.

That is, a phase comparator 58 of the PLL circuit 57 determines a phase difference between the image pickup output and an output of a voltage controlled crystal oscillator (hereinafter referred to as a VCXO) 60 and outputs the phase difference to the VCXO 60 via an LPF 59. The VCXO 60 outputs a reference signal while changing an oscillation frequency so that the phase difference from the phase comparator 58 becomes 0. The reference signal synchronized with the image pickup output is generated by the PLL circuit 57 and given to the signal processing section 54. Thus, it becomes possible to perform signal processing using the reference signal synchronized with the image pickup output in the signal processing section 54.

In the present embodiment, the protection processing section PRc3 configured with a lock detecting section 61 and a time period detecting section 62 are provided in order to enable protection in the C protection mode. In a state where the synchronization of PLL is established, an output of the LPF 59 becomes a predetermined constant voltage. The lock detecting section 61 is given an output of the LPF 59 and can judge whether the PLL circuit 57 is in a locked state or not. A judgment result of the lock detecting section 61 is supplied to the time period detecting section 62.

The time period detecting section 62 detects a time period required until the PLL circuit 57 establishes a lock, by the output of the lock detecting section 61. If the PLL circuit 57 has not been in the locked state for a predetermined time period or more, the time period detecting section 62 judges that an abnormality has occurred in a system and generates a shutdown instruction signal. The shutdown instruction signal from the time period detecting section 62 of the protection processing section PRc3 is supplied to the power generating section P3 via a switch PRS. The switch PRS is adapted to be controlled by the operation controlling section 11.

A memory not shown which stores scope IDs is arranged in the endoscope 40. By the reading section 12 (see FIG. 1) of the processor 50 reading scope IDs from the memory of the endoscope 40, power supply control parameters corresponding to the endoscope 40 are given to the operation controlling section 11 similar as in the first embodiment. By the power supply control parameters inputted to the operation controlling section 11 of the processor 50, the operation controlling section 11 performs control so that power is supplied to the image pickup device 41 in the C protection mode.

That is, the operation controlling section 11 is adapted to switch on the switch PRS if the protection mode is the C protection mode and switch off the switch PRS if the mode is a mode other than the C protection mode. The power generating section P3 is adapted to, when a shutdown instruction signal is given from the protection processing section PRc3, shut down and stop output.

Next, an operation of the embodiment configured as above will be described.

When the endoscope 40 is mounted on the processor 50, the reading section 12 of the processor 50 reads scope IDs from the endoscope 40. Power supply control parameters based on the scope IDs are supplied to the operation controlling section 11. The operation controlling section 11 can grasp a kind of power to be generated and a protection mode for the image pickup device 41 of the endoscope 40 by the power supply control parameters. Note that description will be made on an assumption that a protection mode for power supply to the image pickup device 41 is the C protection mode for causing power supply and supply of a driving signal to the image pickup device 41 to stop when an abnormality is detected.

Now, it is assumed that an abnormality has not occurred in the system, and a shutdown instruction signal has not been given to the power generating section P3. In this case, the power generating section P3 outputs generated power to the image pickup device 41 and the image pickup device driving circuit 56. The image pickup device driving circuit 56 generates a drive signal based on a timing signal from the TG 55 and supplies the drive signal to the image pickup device 41. By being supplied with the power from the power generating section P3 and driven by the drive signal from the image pickup device driving circuit 56, the image pickup device 41 performs image pickup.

An image pickup output from the image pickup device 41 is supplied to the processor 50 via the scope cable 42. The image pickup output is amplified by the amplifier 51, CDS-processed by the CDS circuit 52, converted to a digital signal by the A/D converter 53 and supplied to the signal processing section 54. Further, the image pickup output from the image pickup device 41 is supplied to the PLL circuit 57. The PLL circuit 57 generates a reference signal synchronized with the image pickup output and outputs the reference signal to the signal processing section 54. The signal processing section 54 performs various kinds of signal processing for the image pickup output using the reference signal from the PLL circuit 57 to generate a video signal and output the video signal.

Here, it is assumed that some abnormality occurs in the system, and the PLL circuit 57 cannot be in the locked state. The lock detecting section 61 has detected the locked state by an output of the LPF 59 and outputs a detection result showing that the locked state has not been established to the time period detecting section 62. When a predetermined time period elapses until a lock is established, the time period detecting section 62 judges that an abnormality has occurred in the system and generates a shutdown instruction signal.

When the power supply control parameters were given, the operation controlling section 11 switched on the switch PRS for the power generating section P3 in order to provide protection by the C protection mode. Thereby, the shutdown instruction signal from the time period detecting section 62 is supplied to the power generating section P3 via the switch PRS. Thereby, the power generating section P3 stops output. Thus, if the lock of the PLL circuit 57 is not established within the predetermined time period, shutdown is immediately performed, and power supply to the image pickup device 41 stops. Furthermore, by the stoppage of output of the power generating section P3, the image pickup device driving circuit 56 also stops its operation, and supply of a drive signal to the image pickup device 41 also stops. In this way, protection by the C protection mode is provided.

Thus, in the present embodiment also, advantages similar to those of the first embodiment can be obtained. That is, though it is conventionally necessary to provide a power generating section exclusive for an image pickup device, it is possible to, by selecting a different protection processing section for each of protection modes of control target circuits and causing the protection processing sections to operate, supply power in a protection mode corresponding to the image pickup device using a common power generating section. Further, in the present embodiment, since it is possible to simultaneously stop power supply to two circuits, the image pickup device and the image pickup device driving circuit, it is possible to protect the image pickup device and the like more certainly.

Third Embodiment

Figure 6:
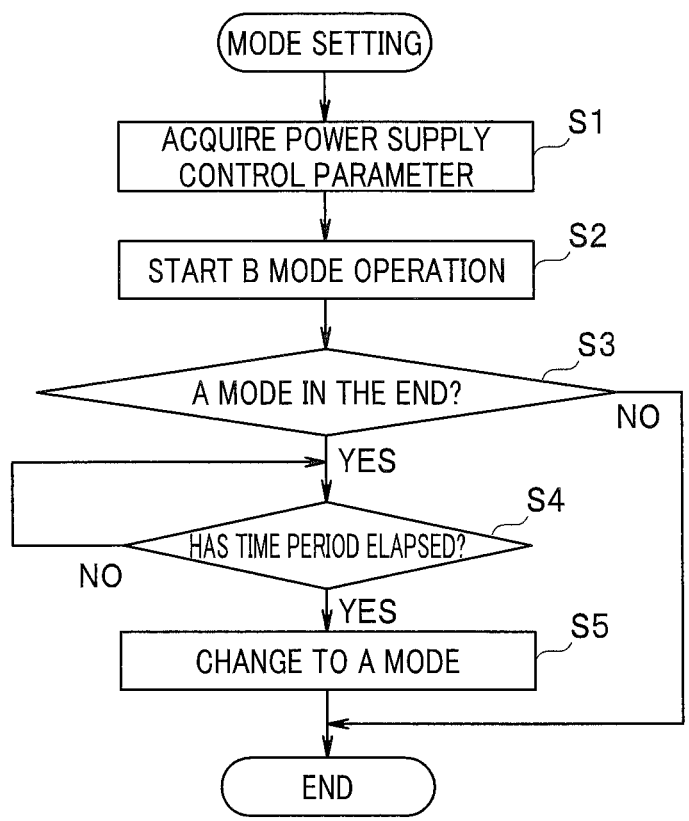
FIG. 6 is a flowchart showing a third embodiment of the present invention.

FIG. 6 is a flowchart showing a third embodiment of the present invention. A hardware configuration of the present embodiment is similar to that of the first embodiment. The present embodiment is different from the first embodiment only in control by the operation controlling section.

In the first embodiment, a protection mode for each power generating section is fixedly decided based on a scope ID. In comparison, in the present embodiment, the protection mode of each power generating section can be changed according to elapse of a predetermined time period or a course of a predetermined sequence.

For example, it is conceivable that an inrush current occurs when operations of the power generating sections P start. In order to prevent the inrush current, a control loop for controlling the variable regulator 32 from the current detecting circuit 31 via the abnormality detecting circuit 33 and the overcurrent protection switching circuit 34 shown in FIG. 2, that is, a constant current control loop is effective. Therefore, by performing overcurrent protection in the B protection mode shown in FIG. 4, the inrush current can be prevented. On the other hand, for example, as for the image pickup device and the like, overcurrent protection in the A protection mode in FIG. 3 for immediately performing shutdown may be preferable.

Therefore, in the present embodiment, the operation controlling section 11 is adapted to be capable of, even in a case of power supply to a circuit required to be immediate shut down, performing power supply in the B protection mode until a predetermined time period elapses after start of an operation and switching to power supply in the A protection mode when the predetermined time period has elapsed. Further, the operation controlling section 11 may detect a course of a predetermined sequence and change the protection mode. For example, at a time of power supply to the image pickup device, the operation controlling section 11 may detect whether a video signal based on an image pickup output is to be outputted or not, perform power supply in the B protection mode until the video signal is outputted, and, when the video signal is outputted, switch to power supply in the A protection mode afterwards.

FIG. 6 shows an example of switching the protection mode according to elapse of a time period. When power is turned on, the operation controlling section 11 acquires power supply control parameters corresponding to scope IDs at step S1 in FIG. 6. Next, the operation controlling section 11 causes the protection circuits PR to select the protection processing sections PRb in the B protection mode and instructs the power generating sections P to generate power. Thereby, the power generating sections P generate power and supply the power to target circuits.

Now, it is assumed that an inrush current is going to be generated by operations of the power generating sections P. In this case, the abnormality detecting circuit 33 detects an overcurrent. Then, the power generating sections P is constant-current-controlled by the protection processing sections PRb, and generation of the inrush current is suppressed.

The operation controlling section 11 judges whether or not the control target circuits are to be overcurrent-protected in the A protection mode in the end, by the power supply control parameters (step S3). If the control target circuits are required to be overcurrent-protected in the A protection mode, the operation controlling section 11 judges at step S4 whether a predetermined time period has elapsed or not. If the predetermined time period has elapsed, the operation controlling section 11 causes the protection circuits PR to select the protection processing sections PRa in the A protection mode and changes an overcurrent-protection mode to the A protection mode at step S5.

Thus, in the present embodiment, it is possible to change the protection mode according to elapse of a time period or a course of a predetermined sequence. Thereby, for example, it is also possible to omit an inrush current preventing circuit.

Fourth Embodiment

Figure 7:
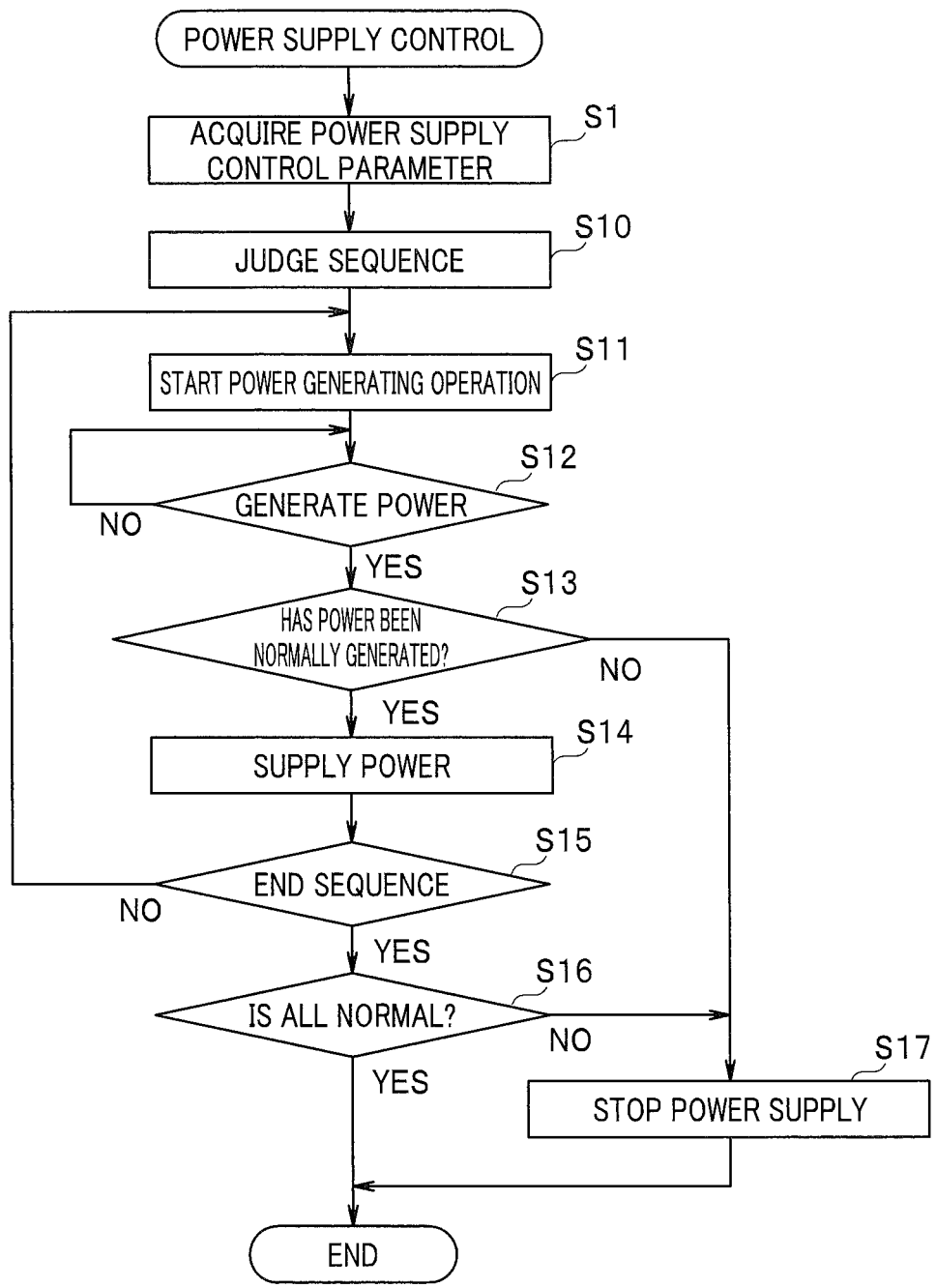
FIG. 7 is a flowchart showing a fourth embodiment of the present invention.

FIG. 7 is a flowchart showing a fourth embodiment of the present invention. A hardware configuration of the present embodiment is similar to that of the first embodiment. The present embodiment is different from the first embodiment only in control by the operation controlling section.

In the present embodiment, an operation of each power generating section is driven in accordance with a predetermined sequence, and each power generating section is caused to sequentially operate while it is judged whether each power generating section is normally operating or not.

At step S1 in FIG. 7, the operation controlling section 11 acquires power supply control parameters corresponding to scope IDs. The operation controlling section 11 judges order of causing the respective power generating sections P1, P2, . . . to be activated and start power supply (a power supply sequence), by the power supply control parameters (step S10).

The operation controlling section 11 causes a first power generating section P in the power supply sequence to start a power generating operation (step S11). At step S12, the operation controlling section 11 is in a waiting state until power is generated from the power generating section P which has been caused to start the power generating operation. In the present embodiment, power supply control is not managed by a time period but managed only by the power supply sequence.

When power is generated from the power generating section P which has started the power generating operation, the operation controlling section 11 judges that power supply is normally performed if voltage of the output is equal to or larger than a predetermined threshold voltage, for example, (rated voltage×0.8), and judges that power supply is not normally performed if the predetermined threshold voltage is not reached. For example, if the operation controlling section 11 is configured with an FPGA, it is possible for the operation controlling section 11 to detect the output voltage of the power generating section P by converting the output of the power generating section P to a digital signal and supplying the digital signal to the operation controlling section 11.

If judging that power supply is not normally performed, the operation controlling section 11 advances the process from step S13 to step S17, stops the operation of the power generating section P and ends the process. If judging that power supply is normally performed, the operation controlling section 11 advances the process from step S13 to step S14 and causes power to be supplied from the power generating sections P to target circuits.

At step S15, the operation controlling section 11 judges whether a power generating operation of a last power generating section P of the power supply sequence has ended or not. If the power generating operation has not ended, the operation controlling section 11 returns the process to step S12 and causes a power generating operation of a next power generating section P of the power supply sequence to start.

After that, a similar operation is repeated. When power from all the power generating sections P is supplied to the target circuits, respectively, the operation controlling section 11 advances the process from step S15 to S16, and judges whether or not all power supply is normally performed in the end. For example, if the operation controlling section 11 detects that voltage of an output of any one power generating section P is equal to or larger than "rated voltage×1.2, the operation controlling section 11 judges that power supply is not normally performed, and causes all the power supply to be stopped at step S17.

Thus, in the present embodiment, order of activating the respective power generating sections is controlled in accordance with a power supply sequence corresponding to an endoscope connected to the processor 10. While confirming that each piece of power has been normally generated, the operation controlling section 11 activates a next power generating section in accordance with the power supply sequence. Thereby, normal power supply voltage is supplied to each target circuit in accordance with the power supply sequence, and a normal operation can be expected in the endoscope.

What is claimed is:

1. An endoscope apparatus comprising:
a plurality of power generating sections configured to supply power to a plurality of target circuits of an endoscope, respectively;
a scope information acquiring section configured to acquire scope information about the endoscope from the endoscope;
a plurality of protection circuits provided in association with the plurality of power generating sections, respectively, wherein each of the plurality of protection circuits is configured to operate in a plurality of protection modes; and
an operation controlling section configured to control the plurality of power generating sections, and to select and set one protection mode from among the plurality of protection modes for each of the plurality of protection circuits based on the scope information.

2. The endoscope apparatus according to claim 1, wherein the operation controlling section is configured to set the one protection mode for the each of the plurality of protection circuits from among the plurality of protection modes based on elapse of a predetermined time period or a course of a predetermined sequence.

3. The endoscope apparatus according to claim 1,
wherein the one of the plurality of protection modes is set so as to, when an abnormality occurs, cause power supply and supply of a drive signal to an image pickup device provided in the endoscope to stop simultaneously.

4. The endoscope apparatus according to claim 1,
wherein the protection circuit comprises:
a current detecting circuit configured to detect a load current flowing through the target circuit; and
an abnormality detecting circuit configured to detect an abnormality in the load current;
wherein the protection circuit is configure to select the one protection mode among the plurality of protection modes based on a detection result of the abnormality detecting circuit to control the power generating section based on the selected protection mode.

5. An endoscope apparatus comprising:
a power generating section configured to supply power to a target circuit of an endoscope;
a scope information acquiring section configured to acquire scope information about the endoscope from the endoscope;

a protection circuit provided in association with the power generating section, wherein the protection circuit is configured to operate in a plurality of protection modes; and an operation controlling section configured to control the power generating section, and to select and set one protection mode from among the plurality of protection modes for the protection circuit, based on the scope information, wherein the protection circuit comprises:
- a lock detecting section configured to detect a lock state of a PLL circuit generating a reference signal synchronized with an image pickup output from an image pickup device provided in the endoscope; and
- a time period detecting section configured to detect a time period until the PLL circuit gets into the locked state, based on a detection result of the lock detecting section;

wherein the protection circuit is configured to select the one protection mode among the plurality of protection modes based on a detection result of the time period detecting section to control the power generating section.

* * * * *